United States Patent [19]
Ramadoss et al.

[11] Patent Number: 5,665,868
[45] Date of Patent: Sep. 9, 1997

[54] CHROMATOGRAPHIC AGENT AND ITS USE FOR THE SEPARATION OR PROTEINS, POLYPEPTIDES OF METALS

[75] Inventors: Candadai Seshadri Ramadoss; Hiten Vasant Lakhey; Patnam Rajagopaliengar Krishnaswamy, all of Bangalore, India

[73] Assignee: Vittal Mallya Scientific Research Foundation, Bangalore, India

[21] Appl. No.: 759,030

[22] Filed: Sep. 13, 1991

[30] Foreign Application Priority Data

Sep. 14, 1990 [GB] United Kingdom ............... 9020098
Jun. 17, 1991 [CA] Canada ............................. 2044717

[51] Int. Cl.$^6$ .................................................. C07K 17/00
[52] U.S. Cl. ..................... 530/412; 530/811; 530/812; 530/352; 530/413; 436/501; 436/86; 436/161; 435/7.8; 435/803; 210/656; 210/767
[58] Field of Search ................. 435/7.8, 803; 530/399, 530/300, 350, 352, 400, 412, 413, 811, 812; 210/656, 660, 681, 767; 436/501, 86, 161

[56] References Cited

U.S. PATENT DOCUMENTS 4,431,546   2/1984   Hughes et al. .................... 210/656

OTHER PUBLICATIONS

Ichihara–Tanaka et al., "Recombinant Carboxyl–terminal Fibrin–binding Domain of Human Fibronectin Expressed in Mouse L Cells", The Journal of Biological Chemistry, Jan. 1990, 265(1):401–407.
Ohana et al., "Comparison of Toxin Binding Sites of the Nicotinic Acetylcholine Receptor from Drosophila to Human," Biochemistry, Mar. 1990, 29(27):6409–6415.
Lewin, 1990, "Genes IV", Oxford University Press, Chapter 29:560–572.
Stryer, 1988, "Biochemistry", Chapter 9:215–216.
Merck Index, Xth Edition, Merck & Co., Rahway, New Jersey, p. 807, item No. 5457.
Linde et al., 1989, Chemical Abstracts 111(1):271, abstract No. 2781q.
Linde et al., 1989, Calcif. Tissue Int. 44(4):286–95.
Alcazar et al., 1988, Neurochem. Res. 13(9):829–836.
Delpech et al., 1986, Analytical Biochemistry 152:100–106.
Grogan et al., 1986, J. Inorg. Biochem. 26(4):237–246.
Muszynska et al., 1986, Biochemistry 25(22):6850–6853.
Riffer, 1986, Chemical Abstracts 105(20):122, abstract No. 174718s.
Riffer, 1986, Proc. Sugar Process Res. Conf. 1984 pp. 231–51.
Yang, 1986, J. Biol. Chem. 261(25):11786–11791.
Nakajo et al., 1984, J. Biochem. (Tokyo) 96(5):1575–1586.
Katoh et al., 1983, Biochim. Biophys. Acta. 760(1):61–68.
Petersen, 1984, Biological Abstracts 78(6), abstract No. 5451.
Petersen, 1983, Eur. J. Biochem. 137(3):531–35.
Clark et al., 1981, Biological Abstracts 72(7), abstract No. 42878.
Clark et al., 1980, Int. J. Biochem. 11(6):577–86.
Woods et al., 1980, Journal of Supramolecular Structure 14:473–480.
Yoshimura et al., 1980, Chemical Abstracts 92(7):234, abstract No. 53700j.
Yoshimura et al., 1979, Biochem. Biophys. Acta 581:316–24.
Thornburg et al., 1978, Journal of Biol. Chem. 253:4638–4641.
Thornburg et al., 1978, Prep. Biochem. 8(2–3):133–146.
Sankaran et al., 1978, Indian J. Biochem. Biophys. 13(1):31–36.
Thornburg et al., 1977, Journal of Biol. Chem. 252:6660–6665.
Shainkin et al., 1971, Biological Abstracts, vol. 52, abstract No. 82061.
Shainkin et al., 1971, J. Biol. Chem. 246(7):2278–84.

Primary Examiner—James C. Housel
Assistant Examiner—Rachel Freed
Attorney, Agent, or Firm—Pennie & Edmonds

[57] ABSTRACT

Phosvitin or a modified phosvitin immobilised and coupled to a suitable matrix may be used for the separation and purification of proteins or polypeptides and in the removal of metal ions from biological material. If desired the phosvitin or modified phosvitin may be in the form of a metal chelate complex.

11 Claims, No Drawings

CHROMATOGRAPHIC AGENT AND ITS USE FOR THE SEPARATION OR PROTEINS, POLYPEPTIDES OF METALS

The present invention relates to separation of polypeptides or proteins or removal of metal ions and to chromatographic agents suitable therefor.

Chromatographic agents for use in various separation processes are well known in the art. However, there has been a tremendous need for chromatographic agents with a specific affinity for proteins. A few proteins such as lectins and protein A are used as ligands for affinity separation. However, their use is limited: lectins can be used only for the isolation and purification of glycoproteins, and protein A only for the isolation and purification of immunoglobulins.

The applicants have discovered that immobilised phosvitin and modified phosvitin act as excellent chromatographic agents for the separation of polypeptides and proteins, especially those that have a high affinity for phospho-serine clusters.

It is known that phosvitin has a high affinity for metal ions. The applicants have found also that this property is also exhibited by immobilised phosvitin, which can be utilised in a system working on the principles of metal-chelate chromatography. Metal ions such for example, as $Fe^{3+}$, $Fe^{2+}$, $Ca^{2+}$, $Mg^{2+}$, $Mn^{2+}$, $Cu^{2+}$, $Co^{2+}$ and $Zn^{2+}$ are all biologically very important because of their involvement in a variety of catalytic processes.

Accordingly, the present invention provides the use of phosvitin or a modified phosvitin for the preparation of a chromatographic agent for the separation and/or purification of polypeptides and proteins or for the removal of metal ions from biological material.

The present invention also provides phosvitin or a modified phosvitin immobilised and coupled to a suitable matrix, for use in the separation and/or purification of polypeptides and proteins.

The phosvitin or modified phosvitin may have been produced by recombinant DNA technology, and the term "phosvitin" as used herein includes both molecules of natural origin and the corresponding recombinant molecules. In the case of a modified phosvitin, the modified molecule itself may be produced by recombinant DNA technology, or recombinant phosvitin may be produced and then modified.

A modified phosvitin may have, for example, one or more of the following modifications while still preserving binding ability: removal of some or all of the carbohydrate; removal of one or more amino acids; addition of one or more amino acids; modification at one or more individual amino acid residues; replacement of one or more individual amino acid residues, for example of aspartic acid by glutamic acid or lysine by arginine; appropriate physical change to the molecule.

If desired, the phosvitin or modified phosvitin may be in the form of a metal chelate complex.

The phosvitin or modified phosvitin may be used in the isolation of polypeptides and proteins, for the separation of various individual polypeptides and proteins from their impurities, and for the purification of polypeptides and proteins. Thus, for example, the chromatographic agent may be used for the resolution of a mixture of proteins or polypeptides from a broth or an extract, and/or it may be used to obtain a protein or polypeptide in a substantially pure (homogeneous) form.

A non-chelated phosvitin or modified phosvitin may also be used for the removal of metal ions from biological material, especially from physiological fluids, for example from blood, serum or plasma.

The present invention further provides a process for the separation and/or purification of a polypeptide or a protein, or for the removal of metal ions from biological material, wherein there is used as chromatographic agent phosvitin or a modified phosvitin, immobilised and coupled to a suitable matrix.

Phosvitin is rich in phosphorylated serine residues and these normally occur in clusters in that protein. Examination of X-ray crystallography data, in relation to proteins having serine clusters, shows that the configuration of those clusters varies greatly from protein to protein, implying, the applicants believe, that the amino acids in proximity to the clusters dictate the configuration those serine clusters can assume.

The applicants have also discovered that proteins such as, for example, cytochrome-C, lysozyme, $EcoR_1$ and human Follicle Stimulating hormone (FSH) have an extremely high affinity for the phospho-serine residues of phosvitin in its immobilised form. These proteins such as cytochrome-C and lysozyme carry charge clusters near their C-terminal regions, and the applicants believe that charge cluster regions which complement certain phospho-serine cluster domains on phosvitin are involved in the observed affinity phenomenon for these proteins.

It is considered that the binding effects observed are not merely the result of a generalised electrostatic interaction between the polyanionic phosvitin molecule and a polycationic protein or polypeptide. It is believed that it is the particular structure and configuration of the phosvitin molecule at and in the region of the phosphoserine clusters that leads to a specific interaction with certain particular proteins and polypeptides that have a complementary structure and configuration at and in the region of charge clusters.

Accordingly, also, we believe, suitable modified phosvitins are especially those retaining the important phosphorylated serine residues, especially those in which some or all, preferably the majority, of the clusters of phosphorylated serine residues are retained. Advantageously, substantially all such clusters are retained.

Further evidence for the postulated involvement of domains in the interaction is given by experiments in which modifications of arginine residues in lysozyme with diacetyl and of lysine residues in cytochrome-C with acetic anhydride were carried out. The applicants have found that these modifications lead to complete loss of the binding property of these proteins to a phosvitin-Sepharose matrix.

Accordingly, polypeptides and proteins that may be separated and/or purified by the non-chelated chromatographic agents according to the invention are especially those having charge clusters, including, for example, various growth factors, DNA binding proteins (those involved in early gene replication and transcription processes) and DNA- and RNA-modifying enzymes. Examples include those given in the following Table 1:

TABLE 1

A. Growth Hormones/Factors:

a) Adrenocorticotropic hormone b) Parathyroid hormone c) Fibroblast growth factors (both acidic & basic)

d) Astroglial growth factors 1 & 2 e) Retina-derived growth factor f) Eye-derived growth factor g) Cartilage-derived growth factor h) Endothelial cell growth factor B. DNA binding proteins:
   a) Proteins having POU domains
   b) Proteins having Homeo domains
   c) Zinc-finger proteins
   d) Leucine Zipper proteins
   e) Amphipathic helix-loop-helix motif-containing proteins
C. DNA-modifying enzymes
D. RNA-modifying enzymes
E. DNA-recombinant fusion protein products:
   Since certain domains in proteins such as cytochrome-C and lysozyme have strong affinity for phosvitin, it is considered that the engineering of the genes corresponding to those domains along with the genes coding for a protein of interest into an organism to produce a fusion protein containing those domains will facilitate their rapid and specific purification using the phosvitin/modified phosvitin chromatographic agent according to the invention, It has been proposed previously to use immobilised phosvitin to purify protein kinases, for which enzymes phosvitin can act as a substrate. Such use is, however, limited to that particular class of enzymes, and is not included in the present invention.

The chemical and structural features of phosvitin in unmodified or modified form that make it eminently suitable for use as chromatographic ligand based, it is believed, on the principle of charge cluster interactions also lend themselves to the generation of metal-chelates.

This ability to form metal chelates is of use, not only for removal of metals from biological and non-biological materials, but also for generation of a metal-chelate chromatographic medium, and this may be used in the separation and/or purification of both biological and non-biological material. Thus, we believe that metal-containing proteins and those having high affinity for metal ions may be purified by metal chelate chromatography.

Thus, for example, the applicants have found that a phosvitin-Sepharose matrix with appropriate chelation with zinc results in a complex which exhibits affinity to proteins: for example it exhibited strong binding of at least two proteins from egg white (110 Kd and 120 Kd). Similarly, chelate complexes with $Fe^{3+}$, $Fe^{2+}$, $Cu^{2+}$ and $Ca^{2+}$ bound, to phosvitin may be prepared and used for the purification of metal-dependant enzymes and other proteins, and an iron chelate complex of phosvitin affinity material may be used to remove peroxides from solvents.

The applicants have also demonstrated high affinity of trypsinised phosvitin towards metal ions. Thus, for example, they have found that trypsinised phosvitin inhibits lipid peroxidation catalysed by Fe-EDTA: 50 mM sodium acetate buffer pH 4.5, 100 micromolar linoleic acid dispersed in Tween 20 and 2–10 μM iron as $FeSO_4$ or Fe(II)-EDTA complex were combined in a total volume of 1 ml. The conjugated diene hydroperoxide formed at 26° C. in this reaction was followed at 234 nm. Addition of 1–5 μg tripsinised phosvitin to the assay system resulted in more than 85% inhibition of the lipid peroxidation under the assay conditions, and if the iron was preincubated with phosvitin then there was total inhibition of the lipid peroxidation, suggesting efficient scavenging of the metal by the modified phosvitin. Likewise, iron(III) chloride added to serum is scavenged by the inclusion of phosvitin. This phosvitin can be precipitated from serum using $CaCl_2$ (10–20 mM).

The high affinity exhibited by phosvitin in unmodified or modified form towards metal ions clearly indicates that the phosvitin matrix may also be used for scavenging excess metal ions including heavy metal ions from physiological fluids, especially blood, for example by haemodialysis. For example, in iron-overload states, the phosvitin matrix may be used, for example for iron scavenging from serum in Cooley's anaemia.

Phosvitin is a naturally-occurring protein, found in avian and fish eggs. Phosvitin can be obtained in purified form (electrophoretically homogeneous) by a number of techniques known per se, for example as described in J. Am. Chem. Soc. [1949] 71, 3670. Thus a chromatographic agent used in the present invention has the advantage that it utilises a protein which is naturally abundant and which can be purified with relative ease.

Advantageously, the β-form of phosvitin may be used; this has a higher phosphate content than the α-form.

The invention includes also the use of modified forms of phosvitin, whether or not prepared from phosvitin itself, and as well as the possibility of using a modified phosvitin ab initio, the possibility of carrying out one or more modifications at any suitable stage in the preparation of the chromatographic agent may be mentioned, The present invention further provides a modified phosvitin having phosphoserine clusters, the structure and configuration of the modified phosvitin molecule at and in the region of the phosphoserine clusters being such that the modified phosvitin molecule is capable of specific interaction with those proteins and polypeptides with which unmodified phosvitin is capable of specific interaction.

Modified phosvitins having affinity for metal ions, for example substantially the same affinity as has phosvitin, should especially be mentioned.

Modification to chain length may be carried out, for example, by chemical and/or enzymatic means, for example proteolysis with the protease trypsin. It is surprising that this proteolysis has proved possible, because it is generally considered that phosvitin is resistant to proteolysis. Phosvitin modified in this way and immobilised on a suitable matrix can have an especially high binding capacity.

Other chemical and/or enzymatic modifications directed at specific amino acid residues are also possible. Furthermore, if the gene for phosvitin, is cloned into another organism to produce a recombinant phosvitin, site-directed-mutagenesis may be used to change a particular amino acid, for example aspartic acid to glutamic acid or lysine to arginine. Such modifications are well-known in molecular biology. If a resulting recombinant phosvitin or modified phosvitin molecule is not already phosphorylated, a phosphorylation reaction should generally be carried out.

The phosvitin or phosvitin modified for example as above may be in the native glycosylated form, or it may be partly or fully deglycosylated. Deglycosylation methods are described in the literature. For removal of asparagine-linked (N-linked) glycosylated moieties see Tarentino A. L., Gomez G. M. and Plummet T. H., (1985), Biochemistry, 24, 4665–4671; for removal of serine-and threontne-linked (O-linked) glycosylated moieties see A. S. B. Edge, et al, (1981), Annal Biochem, 118, 131–137.

Appropriate physical modification of the phosvitin should also be mentioned.

Two or more modifications may be carried out in any suitable order; for example, change of amino acid sequence and/or of chain length may be carried out before or after deglycosylation. Unless the context indicates otherwise, references herein to "phosvitin" are used to include modified phosvitin.

The present invention also provides a modified phosvitin retaining suitability for use in the separation and/or purification of a polypeptide or protein.

The chromatographic agent used according to the invention may be prepared by methods known per se: see, for example "A new method for the analysis of blood serum glycoproteins using Sepharose coupled Lectins", S. Thompson and G. A. Turner, in Lectins, edited by T. C. Bøg-Hansen and D. L. J. Freed, pp 453–458, published by Sigma Chemical Company, 1988. The phosvitin may be attached directly to the matrix or indirectly, by use of spacer arms.

Thus, a chromatographic agent comprising phosvitin or a modified phosvitin immobilized and coupled to a suitable matrix may be prepared by a process comprising mixing the phosvitin with the matrix in the presence of a buffer so that the pH of the mixture is in the range preferably of from 8.0 to 8.3, wishing away the excess ligand of the phosvitin and then blocking the remaining active groups of the matrix by treating the mixture with an amine to produce coupled phosvitin-matrix, washing the resulting product and recovering the coupled phosvitin-matrix.

The matrix may be, for example, a Sepharose gel. We have used CNBr-activated Sepharose and found that it efficiently couples and immobilises phosvitin and modified phosvitin. Activation of Sepharose with cyanogen bromide and coupling of proteins such as lectins to such activated matrix is well known in the art. In addition to cyanogen bromide-activated-Sepharose, other support media/matrices, such, for example, as agarose, acrylamide, silica and suitable fibres (both synthetic and natural) which are appropriately modified to enable coupling of proteins, may be used. The use of spacer arms usually employed for coupling containing 6 to 12 carbon atoms, for example 6-aminohexanoic acid or 1,4-bis(2,3-epoxypropxy)butane, to increase the binding capacities of the affinity material may provide an additional advantage.

The weight ratio of phosvitin to matrix used may be, for example, substantially 0.005:1. The use of 6 to 10 mg of phosvitin per ml of swollen activated Sepharose or other matrix is recommended. The maximum amount of coupling we have observed is about 6 mg/ml; this range of protein gives an affinity product of sufficient capacity for example for purification of proteins.

Mixing of the phosvitin and matrix may be carried out, for example, at a temperature in the range of from 4° to 25° C., more especially at substantially 4° C.

The coupling of the phosvitin to the matrix is carried out in the presence of a suitable buffer. For activated matrices reactive to amine functions, this buffer should preferably be free of primary amines, since if the coupling buffer contains reactive amino groups along with the protein ligand to be coupled, then the extent of protein ligand attachment to the matrix will be reduced, resulting in lower affinity capacity. Any buffer lacking an amino group may be employed, although most preferred are sodium bicarbonate and borate buffers. In general the buffer should provide a pH in the range of from 8.0 to 8.3. Excellent results may be obtained employing sodium bicarbonate buffer containing about 0.5M NaCl. The use of a 0.1M $NaHCO_3$ buffer having a pH of substantially 8.3 and containing 0.5M NaCl should especially be mentioned.

After coupling with the matrix, excess ligands are washed away, for example with the buffer used for the coupling, and as soon as practicable thereafter the remaining active groups are blocked, generally with an amine or an amino acid. Primary amines are preferred. Especially good results have been obtained using ethanol-amine. Amino acids may also be used to block excess reactive sites but are less preferred as these would introduce unwanted charges. The amine may be used, for example, in a concentration of from 0.1 to 1.0M; 1M ethanolamine is especially suitable.

The blocking reaction may be carried out, for example, at a pH of from 7.5 to 9.5, more especially at a pH of substantially 9. It may be carried out, for example, for a period of from 2 to 18 hours, for example for substantially 16 hours. Suitably a temperature in the range of from 4° to 25° C., for example substantially 4° C., is used. Blocking with 1M ethanolamine at a pH of 9 for 16 hours at a temperature of 4° C. should especially be mentioned.

The resulting coupled phosvitin-matrix is then generally washed, to remove non-specifically bound proteins, if any, from the matrix. Usually, two different pHs are used, more especially two or more cycles of alternating pH. The number of cycles is generally three, although the number of such cycles is not critical. Three washing cycles, for example, may be carried out, each cycle consisting, for example, of 0.1M acetate buffer pH 4.0 containing 0.5M NaCl, followed by a wash with 0.1M Tris-HCl pH 8.0 containing 0.5M NaCl. The applicants have found that three such washes generally remove non-specifically bound proteins (if any), from the matrix, as determined by absorbance at 280 nm. The chromatographic agent may then be recovered by filtration. Washing and recovery procedures used in coupling proteins to activated matrices are well known.

Preparation of a chromatography column may then be carried out by known methods. For example, after packing a suitable column with the phosvitin matrix, equilibration may be carried out for example with Tris HCl buffer, suitably with 10 to 50 mM Tris HCl, pH 7.5 to 8.5; a suitable flow rate is 0.25 ml/min.

To prepare a metal chelate, the column after equilibration may be treated with a suitable buffer containing metal ions; usually the same buffer used for equilibration is used in this step, for example 10 mM Tris buffer, pH 7.5, containing, for example, 0.1M zinc acetate, 0.1M ferric chloride or 0.1M calcium chloride. Two to three column volumes of such metal salt-containing buffer is suitably passed through the column, and the column then equilibrated with buffer alone.

Preparation of beads carrying a metal chelate, for example an iron chelate, for example for peroxide removal from solvents, should also be mentioned. Methods for the production of such beads are described in the literature.

The present invention also provides a chromatographic agent which comprises phosvitin in the form of a metal chelate complex, immobilised and coupled to a suitable matrix, and a chromatographic agent which comprises a modified phosvitin, if desired in the form of a metal chelate complex, immobilised and coupled to a suitable matrix, and a process for their preparation as described above.

The actual process for the separation or purification of proteins/polypeptides or for the removal of metal ions may be carried out according to methods known per se, using set protocols, for example as follows.

A column is prepared and equilibrated as described above. The column is then loaded with the crude material (containing for example 1.0 to 5.0 mg/ml protein or the metal-containing material), centrifuged for example at 10,000 rpm for a period of, for example, 10 to 30 minutes, suitably at 4° C. The column is then washed with the equilibration buffer until all non-binding proteins are washed, and the column is eluted, for example with Tris HCl buffer, suitably with 10 to 50 mM Tris HCl, pH 7.5 to 8.5, with a linear gradient of 0.1M to 2M NaCl. A fraction of suitable volume is collected, the wash and eluants being monitored with absorbance at 280 nm. For a metal chelate complex, the pH of the buffer is generally lowered to obtain solution. For scavenging metals, there is generally no elution by salt, although if proteins are bound along with salt elution may be necessary.

Accordingly, the present invention especially provides a process for the separation and/or purification of a polypeptide or protein, especially one having affinity for phosphoserine, which comprises loading the polypeptide or protein onto a chromatographic column containing a chromatographic agent comprising phosvitin or a modified phosvitin, immobilised and coupled to a suitable matrix, previously equilibrated with an equilibrating agent, and eluting the column with a salt solution to obtain the polypeptide or protein.

For example, for purification of lysozyme derived from egg white, the equilibrating agent may be 66 mM $KH_2PO_4$ at a pH of 6.24, and the buffer employed for the elution may be 100 mM $KH_2PO_4$ at a pH of 6.24 containing 200 mM NaCl.

For purification of a restriction enzyme, the equilibrating agent may be, for example, 10 mM Tris-HCl having a pH of 7.5 and containing 50 mM NaCl, 5 mM $MgSO_4$ and 1 mM DTT, and the salt solution may be, for example 10 mM Tris-HCl having a pH of 7.5 and containing 1.5M NaCl, 10 mM KCl, 100 µg/ml BSA and 1 mM DTT.

The column operations are suitably performed at 4° C. In the case of enzymes, activities are determined and for hormones recommended immunoassays are performed.

The following Examples illustrate the invention.

EXAMPLE 1

Purification of Phosvitin

Hen egg yolks were separated and the yolk material was obtained by puncturing the vitelline membrane and draining out the contents. The yolk contents (100 gms) were suspended in 0.11M $MgSO_4$, 5.5 times the volume of the yolk material, and mixed vigorously. The mixture was kept at 4° C. for 18 hours to allow precipitation. The precipitate was dispersed in 70 ml of 0.4M $(NH_4)_2SO_4$ and the ph was adjusted to 4.0. The dispersion was mixed thoroughly and centrifuged. The supernatant was extracted with 30 ml of ether and this was repeated three times. After every extraction the aqueous layer was separated. All aqueous fractions were pooled together and treated with $(NH_4)_2SO_4$ to give 95% saturation. The saturated mixture was allowed to stand at 4° C. overnight.

The precipitated protein was centrifuged and dissolved in water and dialysed against distilled water for 48 hours at 4° C. The water was changed every 8 hours. The dialysed protein solution was lyophilized. Yield:
From 100 gms yolk material 290 mg dry protein were obtained.

The purified phosvitin was then filtered by gel filtration to separate the α and β forms. For this a Sephadex G200 column (104×2.5 cm) was equilibrated with 100 mM sodium acetate buffer pH 5.0 and the dialysed protein (50 mg) were loaded onto the column. The protein in the eluate was monitored by $OD_{280}$. From the analysis of the phosphate content of the protein the second peak corresponded to the β form. The peak fractions were pooled and dialysed against distilled water. The dialysed protein solution was lyophilized of the 50 mg protein loaded 34 mgs were recovered in the peak fractions.

Analysis of phosvitin:
1 Phosphate (inorganic): Phosphate estimation for the protein was done using the Ammonium Molybdate Method (Anal. Chem. [1956] 28, 1756). The digested protein ($H_2SO_4$+$HNO_3$ digestion) was subjected to analysis. The β form had 10.7–11.8% phosphorus.
2 Protein estimation: Lowry's method (J. Biol. Chem. [1951], 193, 265) was used for the protein estimation.

Electrophoretic analysis:
Electrophoresis was done on 10% homogeneous polyacrylamide gel with Tris-glycine buffer pH 8.3. The purified protein showed a single major band. Subsequent analysis on SDS-PAGE showed that the molecular weight of the purified protein was in the range of 30,000 to 35,000. There were no major impurities associated with this protein.

EXAMPLE 2

Preparation of Chromatographic Agent: Immobilisation and Coupling of Phosvitin 3 g of cyanogen bromide-activated Sepharose in freeze-dried powder form were allowed to swell in 1 mM HCl and washed with 1 mM HCl in a sintered glass for 15 min. The gel was then washed with distilled water. Phosvitin (15 mg) in the native glycosylated form prepared in Example 1 was dissolved in 25 ml of 0.1M $NaHCO_3$ pH 8.3 containing 0.5M NaCl. This was mixed with the gel (10 ml) and allowed to rotate gently overnight at 4° C. The excess ligand was washed away with 0.1M $NaHCO_3$ pH 8.3 containing 0.5M NaCl and the remaining active groups were blocked by treatment with 1M ethanolamine pH 9.0 for 16 hours at 4° C. The gel then was washed with three cycles of alternating pH. Each cycle consisted of 0.1M acetate buffer pH 4.0 containing 0.5M NaCl followed by a wash with 0.1M Tris-HCl pH 8.0 containing 0.5M NaCl. The coupled phosvitin-Sepharose was stored at 4° to 8° C. in 100 mM Tris-HC pH 8.0 containing 0.5M NaCl and 0.02% sodium azide and used for the Examples described below.

EXAMPLE 3

Illustration of the Binding Capacity of the Phosvitin-Sepharose Chromatographic Agent 1 ml bed volume columns of the phosvitin-Sepharose chromatographic agent were used, which had been equilibrated with 50 mM Tris-HCl at a pH of 7.5.

To one such column, 0.25 mg of cytochrome-C (obtained from horse heart) dissolved in the equilibrating buffer was loaded. The buffer wash showed negligible material absorbing at 410 nm [soret band of cytochrome C]. The protein was eluted from the column with 20 mM sodium phosphate buffer pH 6.5. The recovery in the eluted sample was more than 90%.

In order to check the specificity, cytochrome-C was allowed to react with soluble phosvitin and then loaded on to the phosvitin-Sepharose. The loaded mixture did not bind to the column clearly suggesting that the binding domain on the cytochrome-C is already masked by phosvitin.

This established the efficacy of the column material, viz. phosvitin.

EXAMPLE 4

Purification of Lysozyme from Egg White

A phosvitin-Sepharose 4B column (5 ml bed volume) was used for this purpose. Egg white was diluted in 66 mM $KH_2PO_4$ pH 6.24 to adjust the $OD_{280}$ to approximately 10 per ml. A total of 10 ml of this diluted egg white was directly loaded onto the phosvitin-Sepharose, previously equilibrated with 66 mM $KH_2PO_4$ pH 6.24. The flow rate was maintained at 1 ml per 3 minutes using a peristaltic pump. After the loading was complete, the column was washed with 66 mM $KH_2PO_4$ pH 6.24. When the $A_{280}$ reading was below 0.05 OD, the column was eluted with 100 mM $KH_2PO_4$ pH 6.24 containing 200 mM NaCl. The fractions (1 ml vol) were monitored for $A_{280}$ absorbance as well as enzyme activity.

The enzyme activity was measured in 66 mM $KH_2PO_4$ pH 6.24 containing the requisite amount of *Micrococcus luteus* cell suspension at 25° C. One Unit is defined here as the decrease in the optical density of 0.1/min. at 450 nm under assay conditions.

The total loading in terms of enzyme unit was 4300 with a specific activity of 39.6 units per mg protein. The salt elution gave a recovery of over 70% with a specific activity in the range of 420 and above. The three times recrystallised preparation from Sigma under identical conditions gave a specific activity of 437.

The enzyme preparation Was analysed by sodium dodecylsulphate polyacrylamide electrophoresis and found to contain in addition to lysozyme a small amount of ovalbumin which has a molecular weight of 45,000.

EXAMPLE 5

Binding of ECoRI and Bam HI to Phosvitin-Sepharose 200 units of each of these restriction enzymes obtained from Bangalore Genei Company were loaded onto separate columns of phosvitin-Sepharose 4B, which had been equilibrated with 10 mM Tris-HCl pH 7.5 containing 50 mM NaCl, 5 mM $MgSO_4$ and 1 mM DTT. These enzymes were eluted with 10 mM Tris-HCl pH 7.5 containing 1.5M NaCl, 10 mM KCl, 100 µg/ml BSA and 1 mM DTT. When the salt concentration was 1.0M, there was no enzyme elution. The assay was based on linearization of purified PUC8 plasmid and subsequent electrophoresis of DNA on 1% agarose gel in Tris-Borate EDTA buffer system.

EXAMPLE 6

FSH Binding and Elution

Phosvitin-Sepharose 4B column (0.25 ml bed volume) was used. The column was equilibrated with 10 mM Tris HCl pH 7.75. The Column was loaded with human Follicle Stimulating Hormone (corresponding to 7 units/l). The column was washed with the equilibration buffer and 8 fractions of 0.25 ml were collected. The column was then eluted with 10 mM Tris HCl pH 7.75 containing 1M NaCl and 8 fractions of 0.25 ml were collected. The fractions were subjected to Delfia® assay. FSH was quantitatively recovered in the third fraction of the eluting buffer.

EXAMPLE 7

Affinity of Phosvitin-Sepharose to Adrenocorticotropic Hormone (ACTH)

Phosvitin-Sepharose (0.25 ml bed volume) was equilibrated with 10 mM Tris HCl pH 7.7. 200 µl of ACTH (human) 1 mg/ml was loaded on the column and the column washed with the same buffer. The column was first eluted with 10 mM Tris HCl pH 7.7 containing 1M NaCl. The wash and salt eluates were assayed for ACTH by radioimmunoassay. It was observed that ACTH is bound to the column and is eluted by 1.0M NaCl.

EXAMPLE 8

Affinity of Phosvitin-Sepharose to Parathyroid Hormone (PTH 44-68)

Phosvitin-Sepharose (0.25 ml bed volume) was equilibrated with 10 mM Tris HCl pH 7.7. 200 µl of parathyroid hormone (PTH) (44-68) 872 pmole/l was loaded. The column was first eluted with 10 mM Tris HCl pH 7.7 containing 1M NaCl and the second elution was done with 10 mM Tris HCl pH 7.7 containing 1.5M NaCl. Assay for the wash and salt eluates was done by radioimmunoassay. It was observed that no solution was obtained with 1M NaCl, and 1.5M NaCl was required for eluting PTH from the phosvitin-Sepharose column, indicating strong binding.

It is clear from Examples 7 and 8 that the phosvitin-Sepharose also binds to hACTH and hPTH from serum samples.

EXAMPLES WITH MODIFIED PHOSVITIN

EXAMPLE 9

Modification of Phosvitin

Phosvitin was modified by proteolysis of the native protein with trypsin as follows:

Trypsinisation:

Phosvitin (purified on the Mono Q column on the FPLC system) was taken up in 20 mM Tris HCl pH 7.5 at a concentration of 20 mg/ml and was treated with trypsin (in a phosvitin:trypsin ratio [w/w] of 100:1). The mixture was incubated at 37° C. for 1 hour. On SDS-PAGE the native protein showed 3 major bands around 28–32 kDa. The trypsinised phosvitin showed a major band at 26 kDa and two others corresponding to molecular weights of around 8000–14000.

Purification of trypsinised phosvitin:

The trypsinised phosvitin was subjected to Cu(II) imino di-acetic acid, metal chelation chromatography. For this purpose chelating Sepharose fast flow column (1 ml, Pharmacia) was equilibrated with a solution of 50 mM copper sulphate till the entire column was coloured. The column was then equilibrated with 20 mM sodium phosphate buffer pH 7.5 containing 0.5M NaCl and then it was loaded with 200 µl (2 mg) protein solution. The column was developed with a pH gradient generated using 20 mM sodium phosphate buffer pH 7.5 containing 0.5M NaCl (buffer A) and 200 mM sodium phosphate buffer pH 3.5 containing 0.5M NaCl (buffer B). All operations were performed on the FPLC system (Pharmacia) at 21° C. Some A280 absorbing material (i.e, that absorbing at 280 nm) (peak P1) was eluted in the buffer A wash and later, at the end of the gradient, the ph was continued to be maintained at 3.5 when another protein (peak P2) was obtained. Analysis of these peaks on SDS-PAGE confirmed that peak P2 represents a truncated version of phosvitin which corresponds to a molecular weight of 26000.

Analytical Results:

Although the molecular weight of truncated phosvitin was less by about 4000–5000, compared to the native protein, their phosphate and carbohydrate content remained essentially similar.

EXAMPLE 10

Immobilisation of Truncated Phosvitin

The P2 fraction was dialysed against 5 mM EDTA and then against Milli Q water. The dialysed protein was lyophilized, and covalently attached to CNBr-activated Sepharose (protocol of coupling was the same as described for phosvitin-Sepharose). 1 ml of coupled matrix typically contains 6 mg protein.

The coupled matrix was designated as P2-Sepharose and was tested for its binding characteristics as described below.

EXAMPLE 11

Affinity of Cytochrome-C to P2-Sepharose

The matrix (0.5 ml bed volume) was equilibrated with 20 mM Tris HCl pH 7.5. The column was loaded with 200 μl of 1 mg/ml of horse heart cyrochrome-C (Sigma). The column was washed with the equilibrating buffer till A280 was nearly zero, and then eluted with 20 mM Tris HCl pH 7.5 containing 1M NaCl. The salt-eluted fractions showed the soret band at 410 nm. The sodium dithionite reduction which resulted in the appearance of α, β, & γ bands confirmed the presence of cytochrome-C.

The binding characteristics of cytochrome-C to P2-Sepharose were very similar to those of phosvitin-Sepharose matrix.

EXAMPLE 12

Affinity of Lysozyme to P2-Sepharose

The 0.5 ml bed volume of P2-Sepharose column was equilibrated with 20 mM Tris HCl pH 7.5. The column was loaded with 500 μl of 14 mg/ml lysozyme (Sigma). The matrix was washed with the equilibration buffer till the A280 was zero, and then eluted with 20 mM Tris HCl pH 7.5 containing 1M NaCl. Virtually no A280 absorbing material appeared either in the breakthrough or in the wash fractions. There was essentially total recovery (>85%) of lysozyme in the salt-eluted fractions. The presence of lysozyme in the eluate was confirmed by subjecting the fractions to enzyme assay. P2-Sepharose has a capacity to bind to 13–14 mg of lysozyme per ml of gel bed volume, whereas the equivalent capacity for phosvitin-Sepharose is 5–6 mg/ml.

The column was used for purification of lysozyme from egg white. The crude egg white preparation was diluted to 10 OD (A280)/ml with 20 mM Tris HCl pH 7.5. The P2-Sepharose column (1 ml) was loaded with 50 OD of crude protein. The breakthrough protein did not show any appreciable lysozyme activity, whereas the 20 mM Tris HCl pH 7.5 containing 1.0M NaCl eluates showed very high specific activity.

In one experiment 7.5 mg of lysozyme could be purified with specific activity of 425 u/mg protein (Unit definition: 1 unit of lysozyme causes A450 change of 0.1/min at 25° C. at pH 6.24).

EXAMPLE 13

Purification of EcoR1 on P2-Sepharose

EcoR1 was purified from the extract of strain RY13 of *E. coli*. The extract of *E. coli* (RY13) was prepared according to the following protocol:

The strain was grown on L-broth pH 7.0 (tryptone 10 g/l; NaCl 10 g/l; Glucose 5 g/l and Yeast extract 5 g/l ), till the OD660 was 1.0 to 1.1. The cells were harvested by centrifugation at 10000 rpm for 10 min and washed in TEM (20 mM Tris HCl pH 7.5 containing 2 mM EDTA and 1 mM β-mecaptoethanol). The cells were taken up in TEM and lysed by sonication for 10 min using Sonics and Material; Vibra Cell Microtip. The lysed extract was centrifuged and the supernatant was treated with 5% (final concentration) streptomycin sulphate at 4° C. for 45 min. The solution was centrifuged at 15000 rpm for 15 min. and the supernatant was dialysed against TEM for 24 hours. The dialysed extract had typically 8.0 mg/ml protein.

1 ml P2-Sepharose was equilibrated with TEM buffer, and 2 ml of the extract was loaded on the column. The column was washed with TEM till the A280 was zero and then eluted with TEM containing 1.5M NaCl. To the peak fractions, BSA (bovine serum albumin) was added to a final concentration of 100 μg/ml and the peak fractions dialysed against TEM overnight and assayed for EcoR1 activity.

We have used lambda-DNA digestion assay to detect and quantitate the EcoR1 activity. We can purify typically 5500 units of EcoR1 using 1 ml bed volume of P2-Sepharose.

What is claimed is:

1. A process for the purification of a biological material, which comprises the steps of:
   a. contacting a chromatographic agent comprising a phosvitin-metal chelate complex immobilized and coupled to a matrix effective for chromatography, with a mixture of a biological material comprising a metal-dependent enzyme or a metal-dependent protein, to form a combination complex between said phosvitin-metal chelate complex and said metal-dependent enzyme or said metal-dependent protein, whereby said combination complex is separated from said mixture; and
   b. eluting said metal-dependent enzyme or said metal-dependent protein to obtain said enzyme or protein in purified form.

2. The process according to claim 1 wherein said metal of the phosvitin-metal chelate complex is selected from the group consisting of $Fe^{2+}$, $Fe^{3+}$, $Zn^{++}$, $Cu^{++}$, $Mn^{2+}$ and $Ca^{++}$.

3. The process according to claim 1 wherein said biological material of said mixture is a metal-dependent enzyme.

4. A process for purification of a protein which comprises the steps of:
   a. contacting a chromatographic agent comprising a phosvitin immobilized and coupled to a Sepharose chromatographic matrix with a mixture comprising a protein, said protein selected from the group consisting of egg white lysozyme, EcoRI, BamHI, follicle stimulating hormone, adrenocorticotrophic hormone and parathyroid hormone, to form a complex between said phosvitin and said protein, whereby said complex is separated from said mixture; and
   b. eluting said complex to obtain said protein in purified form.

5. The process according to claim 4 wherein said phosvitin is a 26 kD modified phosvitin that comprises clusters of phosphorylated serine residues.

6. The process according to claim 5 wherein said protein is selected from the group consisting of egg white lysozyme and EcoRI.

7. A process for purification of a biological material which comprises the steps of:
   a. contacting a chromatographic agent comprising a phosvitin immobilized and coupled to a matrix effective for chromatography, with a mixture of a biological material comprising at least one protein or polypeptide, to form a complex between said phosvitin and said protein or polypeptide, whereby said complex is separated from said mixture; and
   b. eluting said complex to obtain said protein or polypeptide in purified form;
   provided that said protein or polypeptide is selected from the group consisting of lysozyme, a growth factor or growth hormone, a DNA modifying enzyme, a DNA binding protein wherein said DNA binding protein is selected from the group consisting of proteins having POU domains, proteins having homeo domains, zinc-finger proteins, leucine zipper proteins and amphipathic helix-loop-helix motif-containing proteins, and a DNA recombinant fusion protein product wherein a protein of interest is fused to a domain of lysozyme comprising charge clusters.

8. A process according to claim 7 wherein the protein or polypeptide does not have phosvitin-specific receptor ligands.

9. A process according to claim 7, wherein said phosvitin is a modified phosvitin.

10. A process according to claim 7, wherein the protein or polypeptide is a lysozyme, a growth hormone, or a DNA modifying enzyme.

11. A process according to claim 7, wherein the protein or polypeptide is selected from the group consisting of lysozyme, ECoRI, Bam HI, FSH, ACTH, or PTH.

* * * * *